US008754217B2

(12) United States Patent
Lopez de Diego et al.

(10) Patent No.: US 8,754,217 B2
(45) **Date of Patent: *Jun. 17, 2014**

(54) NALMEFENE HYDROCHLORIDE DIHYDRATE

(71) Applicants: H. Lundbeck A/S, Valby-Copenhagen (DK); Biotie Therapies Corp., Turku (FI)

(72) Inventors: Heidi Lopez de Diego, Naerum (DK); Carla De Faveri, Farra di Soligo (IT); Florian Anton Martin Huber, Bolzano Vicentino (IT)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/926,427

(22) Filed: Jun. 25, 2013

(65) Prior Publication Data

US 2013/0338365 A1 Dec. 19, 2013

Related U.S. Application Data

(63) Continuation of application No. 13/132,494, filed as application No. PCT/DK2009/050320 on Dec. 4, 2009, now Pat. No. 8,530,495.

(60) Provisional application No. 61/120,132, filed on Dec. 5, 2008.

(30) Foreign Application Priority Data

Dec. 5, 2008 (DK) ................................ 2008 01729

(51) Int. Cl.
*C07D 489/08* (2006.01)

(52) U.S. Cl.
USPC ........................................................... 546/44

(58) Field of Classification Search
USPC ........................................................... 546/44
See application file for complete search history.

(56) References Cited

U.S. PATENT DOCUMENTS 8,530,495 B2 * 9/2013 Lopez de Diego et al. ... 514/282

FOREIGN PATENT DOCUMENTS

| | | | |
|---|---|---|---|
| CN | 1895251 | A | 1/2007 |
| WO | 2008/104736 | A1 | 9/2008 |
| WO | 2008/104738 | A1 | 9/2008 |
| WO | 2008/109156 | A2 | 9/2008 |

OTHER PUBLICATIONS

The United States Pharmacopeia, 1995, USP 23, NF 18, p. 1843-1844.
Harry G. Brittain (ed), 1999, "Polymorphism in Pharmaceutical Solids", Milford, NJ: Marcel Dekker, Inc., pp. 186-194.
Harry G. Brittain (ed), 1999, "Polymorphism in Pharmaceutical Solids", Milford, NJ: Marcel Dekker, Inc., pp. 202-205.
Harry G. Brittain (ed), 1999, "Polymorphism in Pharmaceutical Solids", Milford, NJ: Marcel Dekker, Inc., pp. 235-238.
Harry G. Brittan (ed), 1999, "Polymorphism in Pharmaceutical Solids", Milford, NJ: Marcel Dekker, Inc., pp. 125, 130-132.
Sime et al., 1975, "The Crystal Structure of a Narcotic Antagonist", Acta Cryst. B. 31, pp. 2323-2330.
Byrn et al., 1995, "Pharmaceutical Solids", Pharmaceutical Research, vol. 12(7), pp. 945-954.
Mason, B., et al. 1999, "A double-blind placebo-controlled study of oral nalmefene for alcohol dependence," Archives of General Psychiatry, 56: 719-724, XP009033908.
Byrn et al., 1999, Solid State Chemistry of Drugs, 2nd Edition, chapter 1, pp. 23-25, and chapter 11, pp. 233-247.
Brittain, H., 1996, "Nalmefene hydrochloride," Analytical Profiles of Drug Substances and Excipients, 24: 351-395.
Hahn, E.F., et al, 1975, "Narcotic antagonists, 4, carbon-6 derivatives of n-substituted noroxymorphones as narcotic antagonists," Journal of Medicinal Chemistry, 18(3): 259-262, XP002500023.
Karhuvaara S., et al., 2007, "Targeted nalmefene with simple medical management in the treatment of heavy drinkers: a randomized double-blind placebo-controlled multicenter study," Alcoholism Clinical and Experimental Research, 31(7), 1179-1187.
Farmacia Remington (1985), 17th Edition, Mack Publishing Company, Easton, PA, pp. 1912-1920 (Spanish Language).
Farmacia Remington (1985), 17th Edition, Mack Publishing Company, Easton, PA, pp. 1912-1920 (English Language Translation).
Request Pursuant to Paragraph 30(7) Patent Rules as filed in connection with corresponding Canadian Patent Applicaton No. 2,744,932 , submitted on Aug. 2, 2013.

* cited by examiner

*Primary Examiner* — Charanjit Aulakh
(74) *Attorney, Agent, or Firm* — Mary Catherine Di Nunzio

(57) ABSTRACT

The present invention relates to the Nalmefene hydrochloride dihydrate, methods of manufacturing Nalmefene hydrochloride dihydrate, a pharmaceutical composition comprising Nalmefene hydrochloride dihydrate and a method of treatment comprising administering Nalmefene hydrochloride dihydrate.

28 Claims, 6 Drawing Sheets

NALMEFENE HYDROCHLORIDE DIHYDRATE

CROSS-REFERENCE TO RELATED APPLICATIONS

The present application is a Continuation U.S. application Ser. No. 13/132,494, filed Jun. 22, 2011, which is a §371 U.S. National Stage Application of International Application No. PCT/DK2009/050320, filed Dec. 4, 2009, which claims priority of U.S. Provisional Application No. 61/120,132, filed Dec. 5, 2008 and Danish Application No. PA. 200801729 filed Dec. 5, 2008. Each of these applications is hereby incorporated by reference in its entirety.

The present invention relates to a novel non-hygroscopic form of Nalmefene Hydrochloride, namely Nalmefene hydrochloride dihydrate, in particular for oral dosage forms, and methods for its production.

BACKGROUND

Nalmefene is a known opioid receptor antagonist which can inhibit pharmacological effects of both administered opioid agonists and endogenous produced agonists from the opioid system. The clinical usefulness of Nalmefene as an antagonist comes from its ability to promptly (and selectively) reverse the effects of these opioid agonists, including the often observed depressions in the central nervous system and the respiratory system.

Nalmefene has primarily been developed for use in the management of alcohol dependence, where it has shown good effect in doses of 10 to 40 mg taken when the patient believed drinking to be imminent (about 1-2 hours before drinking) (Karhuvaara et al., *Alcohol. Clin. Exp. Res*., (2007), Vol. 31 No. 7. pp 1179-1187). Additionally, Nalmefene has also been investigated for the treatment of other addictions such as pathological gambling and addiction to shopping. In these developmental programs and testing, Nalmefene has been used, for example as a parental solution (Revex™).

Nalmefene is an opiate derivative similar in structure to the opiate antagonist Naltrexone. Advantages of Nalmefene relative to Naltrexone include longer half-life, greater oral bioavailability and no observed dose-dependent liver toxicity.

Nalmefene differs from Naltrexone by substitution of the ketone group at the 6-position of Naltrexone with a methylene ($CH_2$) group, which considerably increases binding affinity to the μ-opioid receptor. Nalmefene also has high affinity for the other opioid receptors (κ and δ receptors), and is known as a "universal antagonist" for its ability to block all three.

Nalmefene can be produced according to the method described by Hahn et al. (*J. Med. Chem.,* 18, 259-262 (1975), Mallinekrodt (U.S. Pat. No. 4,751,307), and Meltzner et al., (U.S. Pat. No. 4,535,157).

By using the above-mentioned methods, the free base of Nalmefene is obtained, which subsequently can be converted into the hydrochloride salt, by use of conventional methods.

According to Brittain, (*Analytical Profiles of Drug Substances and Excipients* (1996), Vol 24, pp. 351-395) Nalmefene hydrochloride can be recrystallized from water, giving a pure drug substance, which inevitably consists of a monohydrate crystal phase. In the same review the monohydrate phase of Nalmefene hydrochloride is described as essentially non-hygroscopic since it can only sorb up to 1% of adventitious moisture.

The inventors of the present invention have found that, contrary to the literature, Nalmefene hydrochloride as a monohydrate is hygroscopic.

There is therefore a need for providing a novel, stable and non-hygroscopic hydrate form of Nalmefene and methods for its manufacturing.

SUMMARY OF THE INVENTION

The present invention relates to Nalmefene hydrochloride dihydrate represented by the formula

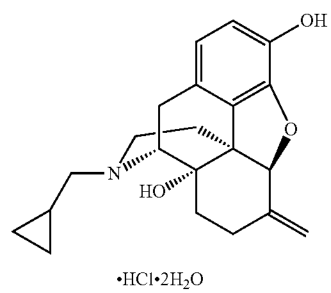 [SMILES: C=C1CC[C@@]2(O)[C@H]3Cc4ccc(O)c5c4[C@@]2(CCN3CC2CC2)[C@H]1O5]

preferably in a crystalline form. Said Nalmefene hydrochloride dihydrate is non-hygroscopic The invention further relates to two methods of producing Nalmefene hydrochloride dihydrate:

Method (I): transformation of Nalmefene hydrochloride into Nalmefene hydrochloride dihydrate by re-slurry in aqueous solution, exemplified by water, such as pure water, and Method (II): recrystallisation of Nalmefene hydrochloride in aqueous solution, exemplified by water, such as pure water.

The re-slurry method (Method I) comprises the steps of:

(1) mixing Nalmefene Hydrochloride (17-(cyclopropylmethyl)-4,5-α-epoxy-6-methylenemorphinan-3,14-diol hydrochloride) and aqueous solution, exemplified by water, such as pure water, (2) optionally, heating the mixture, (3) optionally, distilling the mixture, (4) stirring the mixture until transformation is complete, such as less than 1 hour, such as about 1 hour, such as for at least 1 hour, and (5) isolating the formed solid.

The re-crystallisation method (Method II) comprises the steps of:

(a) mixing Nalmefene hydrochloride (17-(cyclopropylmethyl)-4,5-α-epoxy-6-methylenemorphinan-3,14-diol hydrochloride) and aqueous solution, exemplified by water, such as pure water, (b) heating of the mixture to obtain a substantially homogenous solution, (c) optionally, distillation of the mixture obtained in (b).

(d) cooling of the solution obtained in step (b) or (c), subsequently seeding with Nalmefene hydrochloride, and (e) isolation of the formed solid.

A further aspect of the present invention (Method III) is a method to recover any unused Nalmefene from the methods I and II, comprising the steps of:

(i) optionally, distillation of mother liquors obtained from method (I) or (II)

(ii) basification of the mother liquors obtained in step (i), or from the methods (I) or (II), (iii) extracting the mixture with a suitable organic solvent, (iv) adding hydrogen chloride, and (v) isolating the formed solid The invention further relates to pharmaceutical compositions comprising Nalmefene hydrochloride dihydrate, the use of Nalmefene hydrochloride dihydrate in medicine, and in particular the use of Nalmefene hydrochloride dihydrate for the treatment of alcohol dependency.

DETAILED DESCRIPTION OF THE INVENTION

Figure 1:
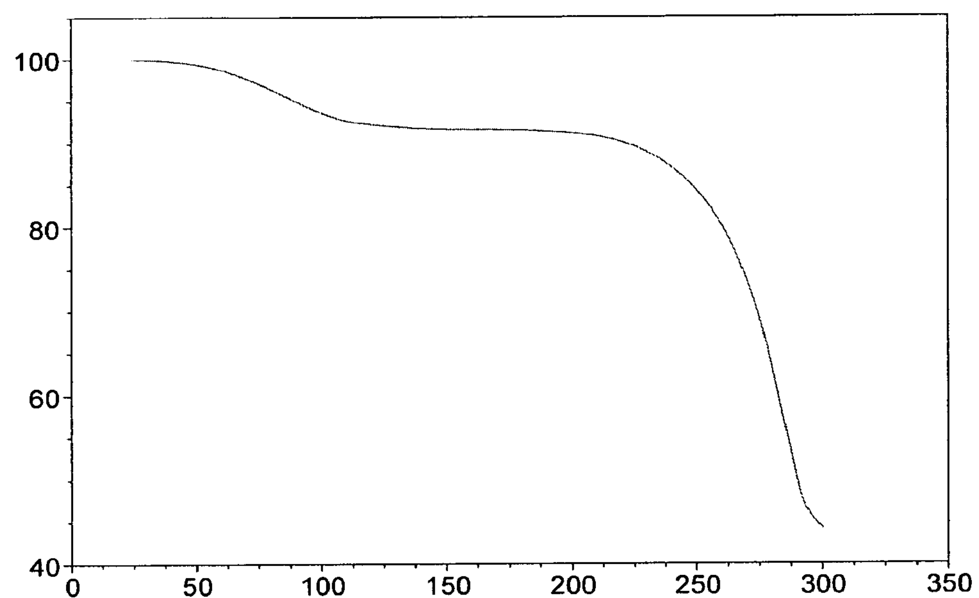
FIG. 1 Shows TGA thermogram of the Nalmefene hydrochloride dihydrate. The y-axis shows the percentage in mass, and the X-axis shows temperatures (° C.).

The present invention relates to Nalmefene hydrochloride dihydrate represented by the below formula

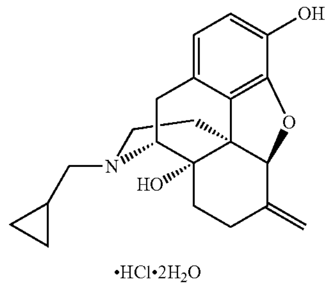 [SMILES: C=C1CC[C@@]2(O)[C@H]3Cc4ccc(O)c5c4[C@@]2(CCN3CC2CC2)[C@H]1O5]

The dihydrate form of Nalmefene hydrochloride is particular advantageous in that it is non-hygroscopic. As a result of this non-hygroscopic feature, the physical properties can more easily be controlled. This is of great importance when preparing solid dosage forms such as orally administrable forms, including solid unit dosage forms e.g. tablets or chewable tablet and capsules.

As is well known within the pharmaceutical industry, processing of hygroscopic products entails the use of controlled humidity chambers both for storage and for the processing itself. Moreover, the finished hygroscopic products must be packed in sealed blisters in order to avoid stability problems due to humidity. These disadvantages are avoided by using Nalmefene hydrochloride as the non-hygroscopic dihydrate.

Nalmefene hydrochloride dihydrate is characterized by being non-hygroscopic and stable in its water content. The compound does not absorb or lose water when exposed to a relative humidity (RH) of between 10% and 95%.

As shown in Example 1 of the present invention, DVS (Dynamic Vapour Sorption) experiments were performed at 25° C. and at 40° C. The results showed that no water was absorbed by Nalmefene hydrochloride dihydrate even at 95% RH. In contrast hereto, as shown in Example 2, Nalmefene hydrochloride as monohydrate absorbed about 2.5% water when exposed to 95% RH and 40° C.

Furthermore, the result in Example 2 showed that in contrast to the dihydrate, the monohydrate form changes in the water content with the surrounding humidity, and at RH above 50% the monohydrate form changed into a new structure with higher water content.

It is therefore an important characteristic of Nalmefene hydrochloride dihydrate that it is non-hygroscopic, as defined above. Thus the present invention relates to Nalmefene hydrochloride dihydrate which is non-hygroscopic, meaning that less than 1%, such as less than 0.5%, such as less than 0.3% moisture is absorbed when exposed to 95% RH at 25° C.

Nalmefene hydrochloride dihydrate is a crystalline solid characterized by X-ray reflections at angles 8.99, 10.63, 15.24, 16.55 and 17.20°2θ (±0.1°2θ) as measured using $CuK_{\alpha 1}$ radiation, and having water content of about 8 to about 9%, such as about 8.7%, while the monohydrate of Nalmefene hydrochloride is a crystalline solid characterized by X-ray reflections at angles 7.39, 11.33, 11.52, 17.70 and 24.27°2θ (±0.1°2θ) and water content of 4-7% depending on the relative humidity of the surroundings.

The present invention also relates to the use of Nalmefene hydrochloride dihydrate in the manufacturing of a medicament.

In particular, the invention is related to the use of Nalmefene hydrochloride dihydrate in the manufacturing of a medicament, wherein Nalmefene hydrochloride dihydrate comprises at least 5% (w/w), such as at least 10% (w/w), at least 30%, at least 50% (w/w), such as at least 70% (w/w), at least 90% (w/w), at least 95% (w/w), at least 99% (w/w), or 100% of the pharmaceutical dosage form, particularly a oral dosage form, e.g. a single unit solid dosage form such as a tablet. Nalmefene hydrochloride dihydrate is in particular related to the use in the manufacturing of a medicament for the treatment alcohol dependency.

In a further embodiment, the present invention relates to a method for treating alcohol dependency comprising administering a therapeutically effective amount of Nalmefene hydrochloride dihydrate, e.g. in a pharmaceutical composition (such as a solid dosage form, e.g. tablet for oral administration) to a patient in the need thereof.

By the term "therapeutically effective amount" is referred to the amount/dose of a compound or pharmaceutical composition that is sufficient to produce an effective response (i.e., a biological or medical response of a tissue, system, animal or human sought by a researcher, veterinarian, medical doctor or other clinician) upon administration to a patient. The "therapeutically effective amount" will vary depending on inter alia the disease and its severity, and the age, weight, physical condition and responsiveness of the patient to be treated. Furthermore the "therapeutically effective amount" may vary if the compound of the invention is combined with one or more compounds, in such a case the amount of a given compound might be lower, such as a sub-effective amount.

The term 'distil' refers to a method of separating mixtures based on differences in their volatilities in a boiling liquid mixture. Application of vacuum such as partial vacuum is an example of such separation method.

The term 'chemical purity' is given its normal meaning within the art and thus refers to the degree to which an obtained compound is contaminated with impurities. Accordingly, an obtained compound which is at least 98% chemically pure comprises at most 2% of impurities. The chemical purity may be measured by e.g. HPLC.

The term 'assay' refers to the effective content of the desired substance expressed as a weight by weight percentage (w/w %).

The term 'extraction' refers to a liquid-liquid extraction in which the free Nalmefene base is transferred from an aqueous phase to an organic phase.

The term 're-slurry' refers to a process wherein the crystalline material is suspended in a solvent or a solvent mixture at an appropriate temperature whereby the crystalline material partially dissolves and partially crystallises again thus permitting its transformation into the desired form and/or its purification.

KF refers to 'Karl Fisher titration'.

TGA refers to 'Thermo-Gravimetric Analysis'.

DVS refers to 'Dynamic Vapour Sorption'

In the present invention, the term "substantially homogenous solution" is intended to mean a liquid mixture free of visible undissolved material.

In the present invention, the term "seeding" is intended to mean the addition of a small amount of crystals to initiate the precipitation of the product.

In the present context the term "non-hygroscopic" is intended to mean that less than 1%, such as less than 0.5%, such as less than 0.3% w/w of moisture is absorbed when exposed to 95% RH at 25° C.

In the present context, particle sizes are determined by Laser Diffraction using a Malvern Mastersizer S instrument as disclosed in details in the introductory part of the experimental section.

Preferably the amount of Nalmefene hydrochloride dihydrate in a pharmaceutical composition is in an amount from about 10 mg to about 100 mg, such as about 10 mg to about 60 mg, about 10 mg to about 40 mg, or about 20 mg.

The term "alcohol dependency" is a commonly known term for a skilled person which, in the revised 4th edition of the Diagnostic and Statistical Manual of Mental Disorders (DSM-IVTR) (*Diagnostic and Statistical Manual of Mental Disorders,* 4th edition text revision, American Psychiatric Publishing, 2000), is defined as the presence of three or more of the seven areas of life impairment related to alcohol in the same 12-month period. These impairments include tolerance, evidence of a withdrawal syndrome when alcohol is discontinued or intake is decreased, potential interference with life functioning associated with spending a great deal of time using alcohol and returning to use despite evidence of physical or psychological problems.

The pharmaceutical composition comprising Nalmefene hydrochloride dihydrate may further comprise one or more pharmaceutically acceptable carriers.

Methods for the preparation of solid pharmaceutical preparations are well known in the art. See, e.g., Remington: The Science and Practice of Pharmacy, 21st ed., Lippincott Williams & Wilkins (2005). Solid preparations, such as tablets, may be prepared by mixing the active ingredients with an ordinary carrier, such as an adjuvant and/or diluent, and subsequently compressing the mixture in a tabletting machine. Non-limiting examples of adjuvants and/or diluents include: corn starch, lactose, talcum, magnesium stearate, gelatine, lactose, gums, and the like. Any other adjuvant or additive such as colourings, aroma, and preservatives may also be used provided that they are compatible with the active ingredients. The pharmaceutical compositions of the invention thus typically comprise an effective amount of Nalmefene hydrochloride dihydrate and one or more pharmaceutically acceptable carriers.

According to the present invention, it is envisaged that Nalmefene hydrochloride dihydrate may be administered in any suitable way, e.g., orally or parenterally, and it may be presented in any suitable form for such administration, e.g., in the form of tablets, capsules, powders, syrups or solutions or dispersions for injection. In an embodiment, Nalmefene hydrochloride dihydrate is preferably administered in the form of a solid pharmaceutical entity, suitably as a tablet or a capsule.

A further aspect of the present invention relates to methods for obtaining Nalmefene hydrochloride dihydrate. Nalmefene hydrochloride dihydrate may be obtained by any of the methods (I) and (II), as will be outlined below.

Method (I) transformation of Nalmefene hydrochloride into Nalmefene hydrochloride dihydrate by re-slurry in aqueous solution, such as water, such as pure water and Method (II) re-crystallization of Nalmefene hydrochloride in aqueous solution, such as water, such as pure water According to One Aspect of the Invention, the Re-Slurry Method (Method (I))

comprises the steps of:

(1) mixing Nalmefene Hydrochloride (17-(cyclopropylmethyl)-4,5-α-epoxy-6-methylenemorphinan-3,14-diol hydrochloride) and aqueous solution, such as water, such as pure water (2) optionally, heating the mixture, (3) optionally, distilling the mixture (4) stirring the mixture, and (5) isolating the formed solid.

In one embodiment of Method (I), Nalmefene hydrochloride is transformed into Nalmefene hydrochloride dihydrate by re-slurry in aqueous solution. In another embodiment Nalmefene hydrochloride is transformed into Nalmefene hydrochloride dihydrate by re-slurry in water. In yet another embodiment Nalmefene hydrochloride is transformed into Nalmefene hydrochloride dihydrate by re-slurry in pure water.

The ratio of aqueous solution such as water, such as pure water, used in step (1) may range from about 0.5 ml to about 4 ml aqueous solution/nalmefene hydrochloride (g), such as from about 1 ml to about 2 ml aqueous solution/nalmefene hydrochloride (g), more preferably about 1.5 ml aqueous solution/nalmefene hydrochloride (g). The Nalmefene hydrochloride used can be selected from any hydrated or solvated form of Nalmefene or mixtures of hydrated and/or solvated forms with or without solvents. In one embodiment Nalmefene hydrochloride as monohydrate is used. In another embodiment of Method (I), Nalmefene hydrochloride is used in hydrated form. In another embodiment, Nalmefene hydrochloride is used in solvated form. In yet another embodiment, Nalmefene hydrochloride is used in a mixture of hydrated solvated form.

In an embodiment of Method (I), solvents comprised in said hydrated and/or solvated forms are selected from the group consisting of acetone, n-propanol, isopropanol, dichloromethane and water. In one embodiment said solvent is acetone. In another embodiment said solvent is n-propanol. In yet another embodiment said solvent is isopropanol. In yet another embodiment said solvent is dichloromethane. In yet another embodiment said solvent is water.

Heating in step (2) is an optional step, which may under some conditions be beneficial in order to increase the dissolution rate of the mixture obtained in step (b). The heating temperature may depend on the circumstances. Under some circumstances the mixing will be efficiently performed at room temperature (20-25° C.). It is envisaged that in one embodiment heating in step (2) is to about 50° C. In another embodiment, heating in step (2) is to 50° C. or less. In another embodiment heating to in step (2) is to about 20° C. to about 40° C. In yet another embodiment heating in step (2) is to about 30° C.

Step (2) and step (3) may be performed with or without stirring.

The distillation in step (3) may be performed to remove organic solvents if present in the mixture. The distillation may be performed by applying Vacuum.

The stirring in step (4) may be performed at a temperature of about 0° C. to about 50° C., such as 45° C., such as from 20° C. to about 40° C. In one embodiment, the mixture is stirred for less than one hour. In another embodiment the mixture is stirred for about one hour. In yet another embodiment the mixture is stirred for at least one hour.

The solid can be isolated at a temperature within the range of about 0-25° C. such as 0-20° C. and more preferably in the range of 0-5° C. in order to lower the solubility of the product, such as in water, and to increase the yield. The solid may be isolated by filtration and washed with a suitable solvent. Solvents for washings include water and mixtures of water/organic solvents or pure organic solvents. Preferably water is used and in a further embodiment pre-cooled water is preferred. When organic solvents are used, Class 2 or 3 solvents (ICH Q3C(R4) guidelines) are preferred. In one embodiment, class 3 solvents such as acetone and ethyl acetate are used. In one embodiment acetone is used. In another embodiment ethyl acetate is used.

The product can be dried under vacuum below 40° C. and more preferably at a temperature in the range 25-35° C.

It is envisaged that the obtained compound is at least 98% chemically pure, such as at least 99% chemically pure, or at least 99.5% chemically pure.

According to One Aspect of the Invention, the Re-Crystallization Method (Method (I))

comprises the steps of:

(a) mixing Nalmefene hydrochloride (17-(cyclopropylmethyl)-4,5-α-epoxy-6-methylenemorphinan-3,14-diol hydrochloride) and aqueous solution, such as water, such as pure water, (b) heating the mixture to obtain a substantially homogenous solution, (c) optionally, distillation of mixture obtained in step (b), (d) cooling of the solution obtained in step (b) or (c), subsequently seeding with Nalmefene hydrochloride, and (e) isolation of the formed solid.

In one embodiment of Method (II), Nalmefene hydrochloride is transformed into Nalmefene hydrochloride dihydrate by re-crystallization in aqueous solution. In another embodiment Nalmefene hydrochloride is transformed into Nalmefene hydrochloride dihydrate by re-slurry in water. In yet another embodiment Nalmefene hydrochloride is transformed into Nalmefene hydrochloride dihydrate by re-slurry in pure water.

The amount of aqueous solution, such as water, such as pure water, which is used in step (a) may range from about 0.9 ml to about 4 ml aqueous solution/Nalmefene hydrochloride (g), such as from about 1 ml to about 2 ml aqueous solution/Nalmefene hydrochloride (g), or about 1.5 ml aqueous solution/Nalmefene hydrochloride (g). The Nalmefene hydrochloride used can be selected from any hydrated or solvated form of Nalmefene or mixtures of hydrated and/or solvated forms with or without solvents.

In one embodiment of Method (II), Nalmefene hydrochloride is used in hydrated form. In another embodiment, Nalmefene hydrochloride is used in solvated form. In yet another embodiment, Nalmefene hydrochloride is used in a mixture of hydrated solvated form.

In an embodiment of Method (II), solvents comprised in said hydrated and/or solvated forms are selected from the group consisting of acetone, n-propanol, isopropanol, dichloromethane and water. In one embodiment said solvent is acetone. In another embodiment said solvent is n-propanol. In yet another embodiment said solvent is isopropanol. In yet another embodiment said solvent is dichloromethane. In yet another embodiment said solvent is water.

The suspension may be heated until a substantially homogenous solution is obtained, i.e. a solution. The heating in step (b) may be performed to reach a temperature of about 50° C. to about 100° C., such as about 50° C. to about 90° C., or about 70° C. to about 85° C.

Partial vacuum may then applied to remove traces of organic volatiles, if present, in step (c).

The solution obtained either from step (b) or step (c) may optionally be filtered (e.g. through a 0.65 μm cartridge) to remove foreign matters before proceeding to step (d).

In step (d) the solution may be cooled to a temperature between 40° C. to about 50° C. and seeded. In one embodiment of the invention, the seeding is performed at a temperature between 40° C. and 50° C. The seeding is performed with Nalmefene hydrochloride dihydrate crystals. The Nalmefene seeding material may, in one embodiment of the invention, be obtained by the re-slurry method (I) described above.

The amount of seed crystal added in step (d) may be from about 1/2000 (w/w) of seed crystal of Nalmefene hydrochloride/Nalmefene hydrochloride added in step (a), such as from about 1/1000 (w/w) of seed crystal or 1/200 of seed crystal of Nalmefene hydrochloride/Nalmefene hydrochloride added in step (a).

An appropriate cooling ramp, such as a fast cooling ramp, and an appropriate stirring, such as a vigorous stirring, impede the crystals already formed to grow further and help to provide a product with a well defined, narrow and relatively small particle size. The cooling from seeding temperature to isolation temperature may be accomplished within a few hours and more preferably within 1 hour. The seeded mixture obtained in step (d) may therefore further be subjected to a cooling, such as a fast cooling, which comprises the steps of:

(d') a further cooling of the mixture to a temperature of about 0-5° C. such as over a time period of about 45 minutes or more, and (d") thereafter the mixture may be maintained at a temperature of about 0-5° C. for e.g. about 45 minutes or more before isolating the formed solid according to step (e).

The solid formed in step (c) may be isolated. The solid can be isolated at a temperature within the range of about 0-20° C. and more preferably in the range of 0-5° C. in order to lower the solubility of the product in water and thereby increase the yield. The solid may be isolated by filtration and washed with a suitable solvent. Solvents for washings include water and mixtures of water/organic solvents or pure organic solvents. In one embodiment solvents for washing are selected from the group consisting of acetone and water. In one embodiment acetone is used. In another embodiment a mixture of acetone and water. In yet another embodiment water is used. In a further embodiment the water used is pre-cooled water. When organic solvents are used for washing, Class 2 or 3 solvents (ICH Q3C(R4) guidelines) are preferred, more preferably class 3 solvents such as acetone and ethyl acetate. In one embodiment ethyl acetate is used.

The product can be dried under vacuum below 40° C. and more preferably at a temperature in the range 25-35° C.

It is envisaged that the obtained compound is at least 98% chemically pure, such as at least 99% chemically pure, or at least 99.5% chemically pure.

It is further envisaged that the Nalmefene hydrochloride dihydrate obtained by the above method (II) has the following particle size distribution: D90 equal to or below 400 μm and D50 equal to or below 200 μm, and D10 equal to or below 50 μm, and with ratio D90/D50 equal to or below 2.5, wherein D"XX" (XX is given as 10, 50 or 90) is defined as the value for which an "XX percentage" (given in volumes) of the particles have a diameter under the indicated value. Thus for D10, 10 percentage of the particle size (in volume) has a diameter equal to or below 50 μm.

Recovery of Nalmefene Hydrochloride from Mother Liquors (Method III):

Nalmefene hydrochloride is highly soluble in aqueous solutions such as water, such as pure water, and therefore a part of this material is lost in the mother liquors. To recover any unused Nalmefene hydrochloride from the methods I or II, outlined above, a method for the recovery has been developed that comprises (i) optionally, distillation of mother liquors obtained from method (I) or (II)
(ii) basification of the mother liquors obtained in step (i), or from the methods (I) or (II),
(iii) extracting the mixture with a suitable organic solvent,
(iv) adding hydrogen chloride, and
(v) isolating the formed solid The basification in step (ii) is performed to bring the pH in the range of 8-10, such as 8-9 using an organic or inorganic base. In an embodiment of method (III), the basification in step (ii) is performed with ammonium hydroxide.

In the extraction step (iii) the organic solvent may be selected from the group comprising halogenated hydrocarbons, ethers, esters, ketones, and preferably dichloromethane, 2-methyl-tetrahydrofurane, ethyl acetate, 2-butanone, even more preferably dichloromethane. In one embodiment the organic solvent is halogenated hydrocarbons. In another embodiment the organic solvent is ethers. In another embodiment the organic solvent is selected from the group of esters. In another embodiment the organic solvent is selected from the group of ketones. In another embodiment the organic solvent is dichloromethane. In another embodiment the organic solvent is 2-methyl-tetrahydrofurane. In another embodiment the organic solvent is ethyl acetate. In another embodiment the organic solvent is 2-butanone.

The solution of nalmefene base in an organic solvent obtained in step (iii) is treated with hydrogen chloride to precipitate nalmefene hydrochloride.

The amount of hydrogen chloride added in step (iv) depends on different factors such as the amount of nalmefene in mother liquors used, and will be apparent to a person skilled in the art. After hydrochloric acid is added to the mixture in step (iv) the product is allowed to precipitate.

The precipitated solid may be isolated as described for methods I and II.

It is envisaged that the obtained compound is at least 98% chemically pure, such as at least 99% chemically pure, or at least 99.5% chemically pure.

EXAMPLES

In the present contest, chemical purity is measured by HPLC using the below conditions:

| Chromatographic conditions: | |
|---|---|
| Column: | YMC Basic B-03-5, 5 μm, 250 × 4.6 mm or equivalent |
| Mobile Phase A: | Buffer |
| Mobile Phase B: | Methanol |
| Buffer: | Dissolve 1.1 g of Sodium Octansulfonate (FW 216.28) in 1 L of water. Adjust the pH to 3.8 with diluted $H_3PO_4$. |
| Column Temperature: | 35° C. |
| Detector: | UV at 230 nm |
| Flow: | 1.5 ml/min |
| Injection volume: | 20 μl |
| Time of Analysis: | 50 minutes |

| Time (min) | Mobile Phase A | Mobile PhaseB |
|---|---|---|
| 0 | 90 | 10 |
| 10 | 70 | 30 |
| 25 | 50 | 50 |
| 40 | 20 | 80 |
| 50 | 20 | 80 |

In the present context, particle sizes are determined by Laser Diffraction using a Malvern Mastersizer S instrument made up of a laser transmitter (LASER HELIUM-NEON-wavelength 632 nm), an optical system (300 F lens, range 0.5-900 μm), a measurement cell for suspension (beam length 2.4 mm) and a photodiode detector. The sample is analysed using mineral oil (CAS 8042-47) as dispergent.

Example 1

1.1a Preparation of the Dihydrate

Dihydrate was prepared as follows:

20 g of crude Nalmefene Hydrochloride (chemical purity 99.26%, assay 92.9%) was suspended in 24 ml of water. The mixture was heated up and the solid dissolved completely at 60-65° C. The solution was heated up to 70° C. and maintained at that temperature for 15 minutes. The solution was cooled down from 70° C. to 20° C. in 3 hours using a linear ramp.

At 50° C., Nalmefene Hydrochloride was added as seeding. The seed did not dissolve and Nalmefene started to crystallize. When the cooling ramp was terminated the suspension was maintained under stirring at 20° C. for 2.5 days. The solid was filtered and washed with acetone (50 ml). The wet product was dried overnight under vacuum at 40° C. yielding 13.2 g of Nalmefene hydrochloride dihydrate (chemical purity 99.74%, water content 8.54% w/w as measured by Karl Fisher titration).

1.1b Preparation of the Dihydrate 20 g of crude Nalmefene Hydrochloride (chemical purity 97.2%, assay 82.6%) was suspended in 30 ml of water. The mixture was heated up and the solid dissolved completely at 80° C. Organic volatiles were removed by vacuum distillation. The solution was cooled down to 50° C.

At 50° C., Nalmefene Hydrochloride dihydrate was added as seeding. The mixture was maintained at 50° C. for 3 hours and then allowed to cool down to 20° C. The suspension was maintained under stirring at 20° C. for around 2.5 days. The solid was filtered and washed with acetone (20 ml). The wet product was dried overnight under vacuum at 30° C. yielding 11.5 g of Nalmefene hydrochloride dihydrate (chemical purity 99.78%, water content 8.78% w/w as measured by Karl Fisher titration).

1.2 Properties of the Dihydrate

In the TGA (FIG. 1) about 10 mg of sample was heated 10°/min in an open pan under nitrogen flow. The thermogram shows a weigh-loss of about 8.5% starting at 0, room temperature and ending at 125-150° C.

Figure 2:
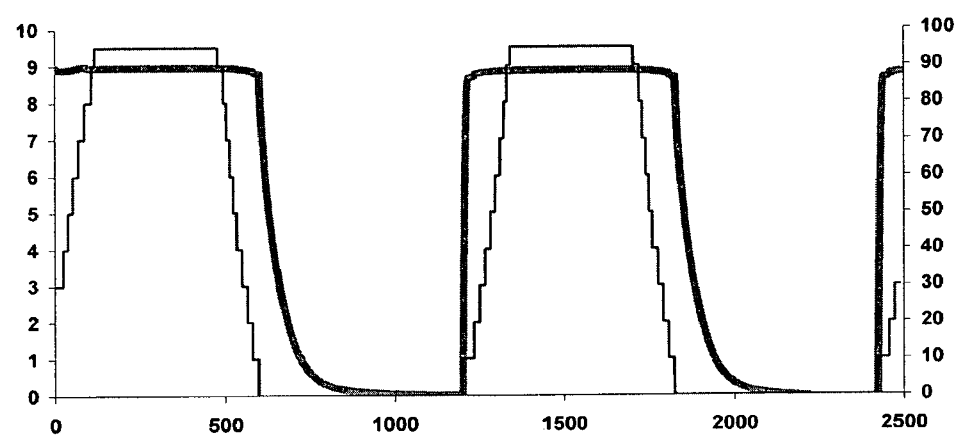
FIG. 2 Shows DVS experiments performed at 40° C. of Nalmefene hydrochloride dihydrate (dry plot). The first y-axis (left) show the change in mass relative to anhydrous (%), and the other y-axis (right) displays the targeted relative humidity (RH)(%), while the x-axis show the time in minutes. The thin line shows the changes in target RH, and the bold line the changes in relation to mass.

DVS experiments were performed at 25° C. and at 40° C. The shape of the curves were the same at the two temperatures; the curve at 40° C. is shown in FIG. 2. The dihydrate is retained at relative humidity of 10-95%. Adsorption to the surface at high relative humidity is less than 0.2%. Desorption of the crystal water occurs slowly under 10% RH. The DVS-curve however shows complete rehydration after drying at 0% RH, thus the crystal lattice is retained by this treatment.

Figure 3:
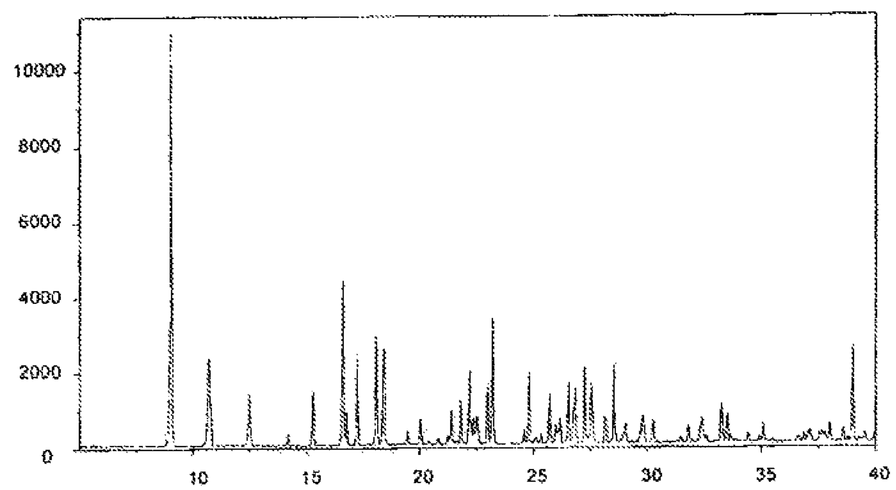
FIG. 3 Shows X-ray powder diffractogram of the Nalmefene hydrochloride dihydrate. The y-axis shows the intensity (counts), and the x-axis shows the 2Theta angle (°).

X-ray powder diffractogram for Nalmefene hydrochloride dihydrate as obtained using Cu $K_{\alpha1}$ radiation is shown in FIG. 3. The diffractogram is measured in reflection mode in the range 5-40°2θ. It is characterised by XRPD reflections at 8.99, 10.63, 15.24, 16.55 and 17.20°2θ (±0.1°2θ).

Example 2

2.1a Preparation of the Monohydrate 25 g of Nalmefene hydrochloride (chemical purity 99.24, assay 84.1) was suspended in 32 ml of water. The mixture was heated up to 80° C. Vacuum was applied to distill low boiling organic solvents. The solution was cooled down to 20° C. in one hour using a linear ramp. The suspension was maintained under stirring for two hours and then further cooled to 4° C. in one hour and maintained under stirring at this temperature for one additional. The solid was filtered and washed with 25 ml of acetone. The wet solid was dried overnight under vacuum at 30° C. yielding 13.5 g of Nalmefene hydrochloride monohydrate (water content 4.74% w/w as measured by Karl Fisher titration, yield 61%).

2.1b Preparation of the Monohydrate

In a jacketed reactor nalmefene hydrochloride (72.3 g) and water (100 ml) were charged. The suspension was heated up to 85° C. obtaining a solution. Nitrogen flow was applied. The solution was cooled down to 60° C. in around 50 minutes and then kept at this temperature for 10 minutes. The product started to precipitate at 60° C. The suspension was further cooled to 55° C. and maintained at 55° C. for 10 minutes. The suspension was cooled to 8° C. in around one hour and maintained at that temperature for 30 minutes before isolation. The solid was filtered and washed with 83 ml of acetone. The solid was dried yielding 48.6 g of nalmefene hydrochloride monohydrate.

2.2 Properties of the Monohydrate

Figure 4:
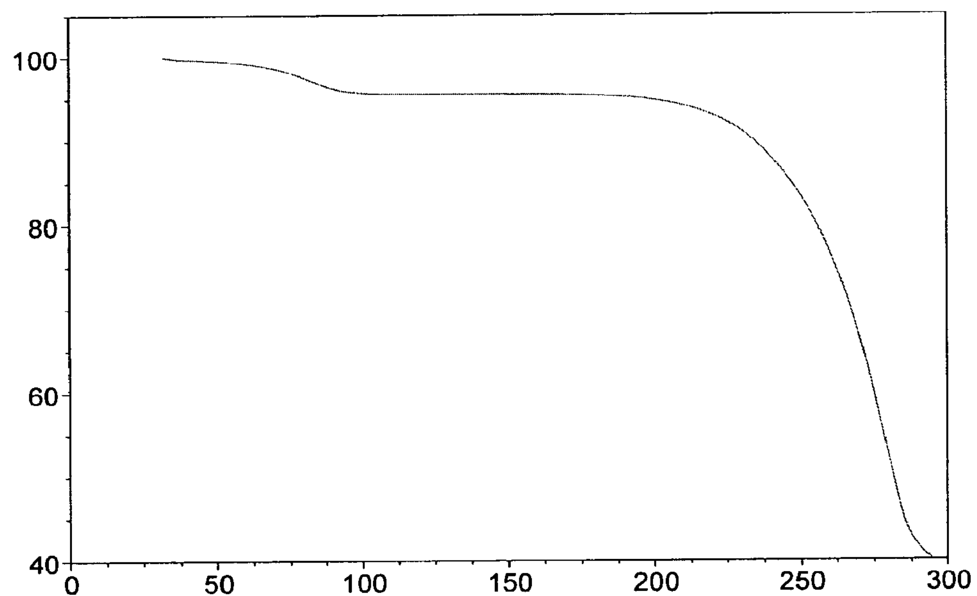
FIG. 4 Shows TGA thermogram of the Nalmefene hydrochloride monohydrate. The y-axis shows the percentage in mass, and the x-axis shows temperatures (° C.).

In the TGA (FIG. 4) about 5 mg of sample was heated 10°/min in an open pan under nitrogen flow. The thermogram showed a weigh-loss of about 4% starting at room temperature and ending at 100-110° C.

Figure 5:
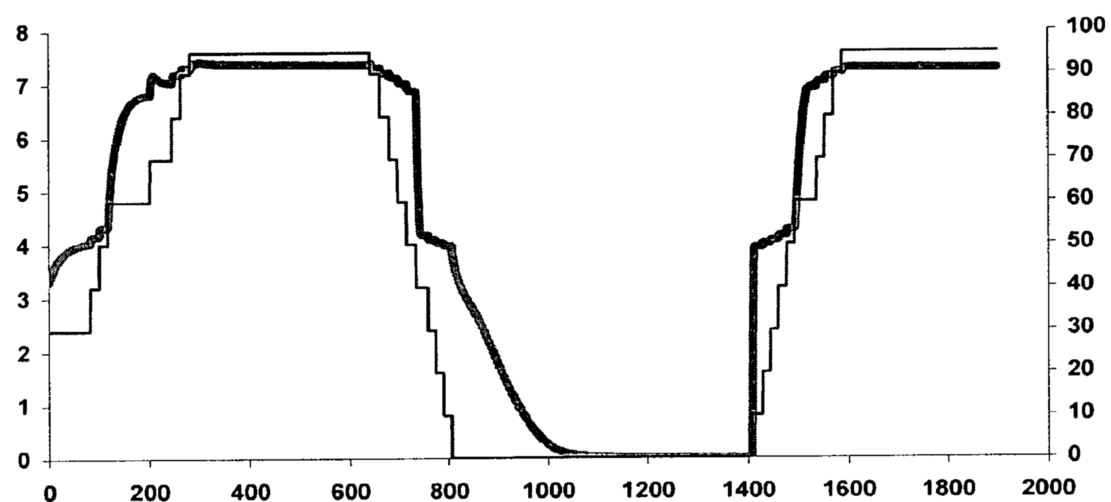
FIG. 5 Shows DVS experiments performed at 40° C. of Nalmefene hydrochloride monohydrate (dry plot). The first y-axis (left) show the change in mass relative to anhydrous (%), and the other y-axis (right) displays the targeted relative humidity (RH)(%), while the x-axis show the time in minutes. The thin line shows the changes in target RH, and the bold line the changes in relation to mass.

DVS experiments were performed at 25° C. and at 40° C. The shape of the curves was the same, only the curve at 40° C. is shown (FIG. 5).

Most of the water of hydration (4%) was absorbed at 10% RH. Then the weight stepwise increased with the humidity up to 4.3% at 50% RH, but at 60% RH it suddenly increased to 6.9% and then again stepwise increased to 7.3% at 95% RH. The amounts here are given as % weigh increase relative to dry, thus the weight gain corresponding to monohydrate was 4.8% and a 1.5 hydrate corresponds to a gain of 7.2%. The curve therefore showed that the water content of the monohydrate was not constant but changes with the relative humidity.

Figure 6:
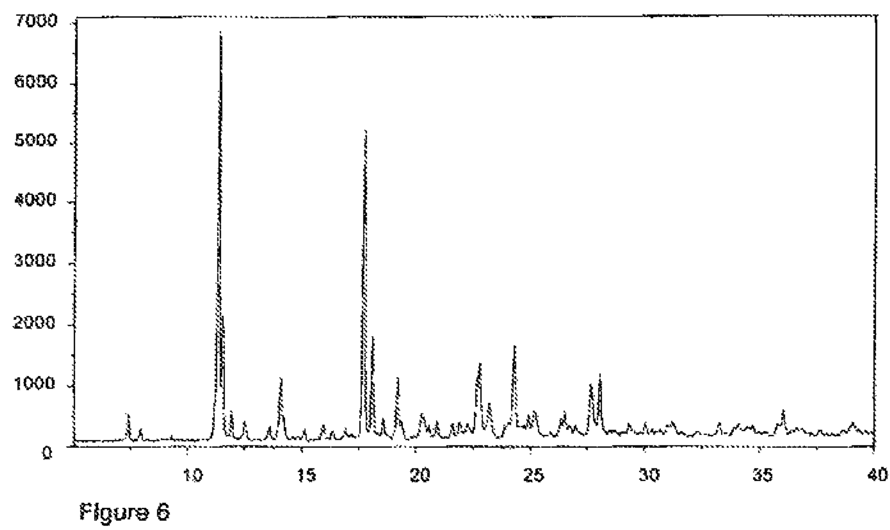
FIG. 6 Shows X-ray powder diffractogram of the Nalmefene hydrochloride monohydrate. The y-axis shows the intensity (counts), and the x-axis shows the 2Theta angle (°).

X-ray powder diffractogram (FIG. 6) for Nalmefene hydrochloride monohydrate as obtained using Cu Kα1 radiation is shown in FIG. 6. The diffractogram is measured in reflection mode in the range 5-40°2θ. It is characterised by XRPD reflections at 7.39, 11.33, 11.52, 17.70 and 24.27°2θ (±0.1°2θ).

Example 3

Preparation of Nalmefene Hydrochloride Dihydrate

Crude Nalmefene hydrochloride (7.67 Kg, assay 93.9%) and water (8.6 liter) were charged into a suitable reactor. The suspension was heated up to 80° C. until the substrate completely dissolved. Vacuum was then applied to remove organic solvents. The resulting solution was then filtered through a 0.65 μm cartridge and then diluted with water (2.1 liter) used to rinse the reactor and pipelines. The solution was cooled down to 50° C. and 7 g of Nalmefene hydrochloride dihydrate seeding material was added. The mixture was cooled down to 0-5° C. in one hour under efficient stirring and then maintained under stirring for one additional hour. The solid was filtered and washed with acetone. The wet product was dried at 25° C. under vacuum to provide Nalmefene hydrochloride dihydrate (5.4 Kg; yield 73%) with a chemical purity of 99.89% (HPLC).

The particle size of the so obtained Nalmefene hydrochloride dihydrate was determined by Laser Diffraction using a Malvern Mastersizer S instrument. Particle size distribution is reported in the table below:

| D10 | D50 | D90 |
|---|---|---|
| 14 μm | 122 μm | 287 μm |

Example 4

Recovery of Nalmefene Hydrochloride

The mother liquors obtained in Example 3 were concentrated under vacuum. Ammonium hydroxide was added till pH 8-9. The mixture was extracted with dichloromethane at a temperature of 30-35° C. The organic phase was separated and cooled down to 25° C. Concentrated hydrochloric acid was added and the product was allowed to precipitate. The solid was filtered and washed with dichloromethane thus giving 1.35 Kg of Nalmefene HCl with a chemical purity of 98.9%, which can be transformed into the dihydrate applying the procedure described in Example 3.

Example 5

Transformation of Nalmefene HCl into Nalmefene HCl Dihydrate by Re-Slurry 50 g Nalmefene HCl (mixture of monohydrate, acetone solvate and dihydrate) was suspended in 50 ml of water at room temperature. Vacuum was applied for one hour in order to remove acetone. The suspension was further stirred at room temperature for two hours. The solid was filtered and dried under vacuum at 30° C. obtaining 39.9 g of pure Nalmefene HCl dihydrate (water content 8.76% w/w as measured by Karl Fisher titration).

Example 6

Transformation of Nalmefene HCl into Nalmefene HCl Dihydrate by Re-Slurry 3.6 g of Nalmefene HCl monohydrate was suspended at room temperature in 5 ml of water. The suspension was stirred at room temperature. The conversion to dihydrate was completed after 1.5 hours.

The invention claimed is:

1. A method for obtaining a compound having the formula

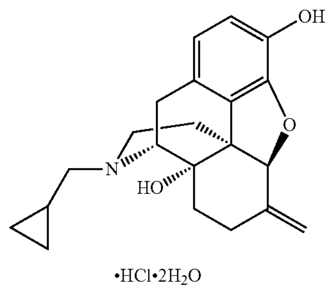 [SMILES: C=C1CC[C@@]2(O)[C@H]3Cc4ccc(O)c5c4[C@@]2(CCN3CC2CC2)[C@H]1O5]

$\cdot HCl \cdot 2H_2O$ comprising the steps of:

(1) mixing Nalmefene Hydrochloride (17-(cyclopropylmethyl)-4,5-α-epoxy-6-methylenemorphinan-3,14-diol hydrochloride) and an aqueous solution, (2) optionally, heating the mixture, (3) optionally, distilling the mixture, (4) stirring the mixture until transformation is complete, and (5) isolating the formed solid.

2. The method according to claim 1 wherein the mixture in (4) is stirred for at least 1 hour.

3. The method according to claim 1, wherein the ratio of the aqueous solution used in step (1) ranges from about 0.9 ml to about 4 ml aqueous solution/Nalmefene Hydrochloride (g).

4. The method according to claim 1, wherein the Nalmefene Hydrochloride used in step (1) is in a hydrated form.

5. The method according to claim 1, wherein the Nalmefene Hydrochloride used in step (1) is in a solvated form or is a mixture of hydrated and solvated forms.

6. The method according to claim 1, wherein stirring is performed in step (2) and/or step (3).

7. The method according to claim 1, wherein the stirring in step (4) is performed at a temperature of about 0° C. to about 45° C.

8. The method according to claim 1, wherein the formed solid in step (5) is isolated at a temperature from about 0° C., to about 20° C.

9. A method for obtaining a compound having the formula

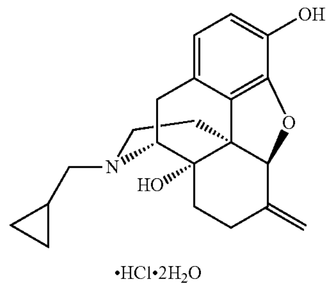 [SMILES: C=C1CC[C@@]2(O)[C@H]3Cc4ccc(O)c5c4[C@@]2(CCN3CC2CC2)[C@H]1O5]

$\cdot HCl \cdot 2H_2O$ comprising the steps of:

(a) mixing Nalmefene hydrochloride (17-(cyclopropylmethyl)-4.5-α-epoxy-6-methylenemorphinan-3,14-diol hydrochloride) and an aqueous solution, (b) heating the mixture of step (a) to obtain a substantially homogenous solution, (c) optionally, distilling the mixture obtained in step (b), (d) cooling the solution obtained in step (b) or step (c), subsequently seeding with Nalmefene hydrochloride, and (e) isolating the formed solid.

10. The method according to claim 9, wherein the amount of aqueous solution used in step (a) ranges from about 0.9 ml to about 4 ml aqueous solution/Nalmefene hydrochloride (g).

11. The method according to claim 9, wherein heating in step (b) is performed to reach a temperature of about 50° C. to about 100° C.

12. The method according to claim 9, wherein the solution in step (d) is cooled to a temperature between 40 to 50° C. and seeding is performed at that temperature.

13. The method according to claim 9, wherein the amount of seed crystal added in step (d) is from about 1/2000 (w/w) of seed crystal of Nalmefene hydrochloride/Nalmefene hydrochloride added in step (a).

14. The method according to claim 9, wherein the Nalmefene used for seeding is Nalmefene hydrochloride dihydrate.

15. The method according to claim 9, wherein the mixture obtained in step (d) comprising the seed crystal(s), is further subjected to:

(d') further cooling the mixture to temperature of about 0-5° C. over a time period of about 45 minutes or more, and (d'') thereafter maintaining the mixture at a temperature of about 0-5° C. for about 45 minutes or more, before isolating the formed solid according to step (e).

16. The method according to claim 9, wherein the solid formed is isolated at a temperature of about 0-5° C. in step (e).

17. The method according to claim 9, wherein the obtained compound has the following particle size distribution: D90 equal to or below 400 μm, D50 equal to or below 200 μm, D10 equal to or below 50 μm, with ratio D90/D50 equal to or below 2.5.

18. The method according to claim 1 further comprising the steps of:

(i) optionally, distilling the mother liquors, (ii) basification of the mother liquors obtained in step (i), above or step (5) of claim 1, (iii) extracting the mixture with a suitable organic solvent, (iv) adding hydrogen chloride, and (v) isolating the formed solid.

19. The method according to claim 18 wherein the basification in step (ii) is performed until the pH is in the range of 8-10.

20. The method according to claim 19, wherein the basification in step (ii) is performed until the pH is in the range of 8-9.

21. The method according to claim 19, wherein the solvent used in the extraction step (iii) is selected from the group consisting of halogenated hydrocarbons, ethers, esters, and ketones.

22. The method according to claim 1, wherein the stirring in step (4) is performed at a temperature of about 20° C. to about 40° C.

23. The method according to claim 9, wherein heating in step (b) is performed to reach a temperature of about 50° C. to about 90° C.

24. The method according to claim 9, wherein heating in step (b) is performed to reach a temperature about 70° C. about 85° C.

25. The method according to claim 9 further comprising the steps of:

(i) optionally distilling the mother liquors, (ii) basification of the mother liquors obtained in step (i) above or step (e) of claim 9, (iii) extracting the mixture with a suitable organic solvent, (iv) adding hydrogen chloride, and (v) isolating the formed solid.

26. The method according to claim 25 wherein the basification in step (ii) is performed until the pH is in the range of 8-10.

27. The method according to claim 26, wherein the basification in step (ii) is performed until the pH is in the range of 8-9.

28. The method accordingly to claim 26, wherein the solvent used in the extraction step (iii) is selected from the group consisting of halogenated, ethers, esters, and ketones.

* * * * *